United States Patent [19]

Khan

[11] Patent Number: 4,976,549
[45] Date of Patent: Dec. 11, 1990

[54] APPARATUS AND METHOD FOR DIRECT MEASUREMENT OF COAL ASH SINTERING AND FUSION PROPERTIES AT ELEVATED TEMPERATURES AND PRESSURES

[75] Inventor: M. Rashid Khan, Morgantown, W. Va.

[73] Assignee: The United States of America as represented by the United States Department of Energy, Washington, D.C.

[21] Appl. No.: 350,815

[22] Filed: May 12, 1989

[51] Int. Cl.[5] ............................................ G01N 25/16
[52] U.S. Cl. ........................................ 374/56; 374/55; 374/21; 324/713; 204/1 T
[58] Field of Search .................... 374/55, 56, 16, 21, 374/22, 23; 204/1 T; 324/713

[56] References Cited

U.S. PATENT DOCUMENTS 3,583,208  6/1971  Byrne, Jr. et al. ................... 374/56

FOREIGN PATENT DOCUMENTS 0920485  4/1982  U.S.S.R. ............................... 374/16

OTHER PUBLICATIONS

Ritter, M. et al., "Volume Expansion of Sodium Near the Melting Point for Different Impurity Contents," J. Applied Physics, vol. 41, No. 13 (Dec. 1970).
Etter, D. E., "A Compact High Temperature Dilatometer," The Review of Scientific Instruments, vol. 41, No. 7 (Jul. 1970).
McKinnon, N. A., "A Combined Dilatometer and Electrical Resistivity Apparatus for Studies in Powder Metallurgy," J. of Scientific Instruments, vol. 31, p. 383 (Oct. 1954).
Khan, R. et al., "Thermoplastic Properties of Coal at Elevated Pressures," Fuel, vol. 63, pp. 109–115 (Jan. 1984).
Ide, T. et al., "The High Pressure and High Temperature Dilatometer," Japan J. Appl. Phys., vol. 16, No. 4 (Apr. 1977).
"Dilatometers by Netzsch," Dynatech Corporation, Models 402, 404, 409, 419, Cambridge, Mass. (Oct. 1967).
Khan, M. R., Jenkins, R. G., Fuel Processing Technology, 1984, 8, 307–311.
Khan, M. R., Jenkins, R. G., Fuel, 1985, 64(11), 1618–1622.
Khan, M. R., Jenkins, R. G., Fuel, 1986, 65(9), 1291–1299.
Khan, M. R., Jenkins, R. G. Fuel Processing Technology, 1986, 17, 63–71.

Primary Examiner—William A. Cuchlinski, Jr.
Assistant Examiner—Diego F. F. Gutierrez
Attorney, Agent, or Firm—David E. Breeden; Stephen D. Hamel; William R. Moser

[57] ABSTRACT

A high-pressure microdilatometer is provided for measuring the sintering and fusion properties of various coal ashes under the influence of elevated pressures and temperatures in various atmospheres. Electrical resistivity measurements across a sample of coal ash provide a measurement of the onset of the sintering and fusion of the ash particulates while the contraction of the sample during sintering is measured with a linear variable displacement transducer for detecting the initiation of sintering. These measurements of sintering in coal ash at different pressures provide a mechanism by which deleterious problems due to the sintering and fusion of ash in various combustion systems can be minimized or obviated.

2 Claims, 4 Drawing Sheets

APPARATUS AND METHOD FOR DIRECT MEASUREMENT OF COAL ASH SINTERING AND FUSION PROPERTIES AT ELEVATED TEMPERATURES AND PRESSURES

BACKGROUND OF THE INVENTION

The present invention relates to apparatus and method for directly measuring ash fusion properties at elevated temperatures and pressures, and more specifically to a high-pressure microdilatometer (HPMD) which measures ash fusion and sintering behavior by independent but simultaneous measurement of expansion/contraction characteristics and electrical resistivity of ash samples at elevated temperature and pressures in oxidizing or reducing atmospheres.

In coal combustion and gasification systems such as fluidized beds, slagging fixed-beds and entrained-flow systems the fusion, sintering, and deposition of ash impose serious operating problems which have been difficult to cope with or overcome. These problems are becoming even more difficult to understand so that suitable corrections may be made due to the trend in using coal conversion systems which operate at relatively high temperatures and pressures. Coal ash has different characteristics when subjected to high temperatures and pressures. For example, in a slagging fixed-bed gasifier coal becomes devolatilized in a highly reducing atmosphere, but the coal ash undergoes fusion at elevated temperature and pressure in an oxidizing atmosphere. The fusibility and sinterability of coal ash critically affect slagging and, hence, fouling in combustors and gasifiers.

Coal ash fusibility has been previously determined by an ASTM test used for evaluating the slagging tendency of coal ash by measuring gross changes in shape of a conical compact of coal particles heated at 80° C. per minute (at 1 atm pressure) in a specified atmosphere. Four characteristic temperatures defining ash fusibility were based on the deformation of the cone with rising temperature: (1) initial deformation temperature where the apex of the cone first becomes rounded; (2) softening temperature where the cone fuses and the height is equal to the base; (3) hemispherical temperature where the height of the cone is equal to half of the base width; and (4) fluid temperature where ash flows into a fluid layer.

It was found that the ASTM technique yielded only the gross tendencies of bulk samples with data likely applying to large ash particles in the conical compact. The "low melting" components providing minor concentrations in the ash may lead to particle-to-particle bonding of fly ash below the melting point temperature of bulk ash so as to prevent the ASTM technique from revealing the fusion and melting behavior of minor, e.g. alkali, components in the ash. Also, the ash melting and fusion process may occur at temperatures differing form those observed by the ASTM technique.

It has been shown that ash resistivity drops suddenly when the temperature of the ash reaches a certain transition temperature, ($T_r$) as discussed in Cumming et al, "An Electrical Resistance Method for Detecting the Onset of Fusion in Coal Ash, "*Fouling and Slagging Resulting from Impurities in Combustion Gases*, R. W. Bryers, ed., New York: Engineering Foundation, 1983, pp. 329–341. This transition temperature which indicates the first presence of a trace liquid phase is invariable below the temperature where initial deformation of the conical compact occurred when using the ASTM technique.

The comparison of sintering point data from both volume change and electrical resistivity measurements has also been used. The sintering points of several coal ashes, except for high sodium North Dakota lignite, have been found to agree closely. Electrical resistivity measurements for high-sodium coal indicates a much lower sintering temperature which was possibly due to an $Na_2O$-induced liquid phase. This technique provided a valuable tool for determining sintering effects due to addition or removal of mineral constituents such as $Na_2O$, and provided for the assessment of models describing vitrification. However, it has been found that no presently available techniques or equipment can provide accurate measurement of the behavior of coal ash at elevated temperatures and pressures.

SUMMARY OF THE INVENTION

While the previous techniques provided some information relating to various properties of coal at elevated temperatures there is presently no apparatus or method for accurately measuring the thermophysical properties of coal ash at elevated temperatures and pressures such as would be present in advanced gasifiers and combustors.

Accordingly, it is an object of the present invention to provide an apparatus and method for directly measuring ash fusion behavior at elevated temperatures and pressures in oxidizing and reducing atmospheres. Generally, the apparatus of the present invention is a microdilatometer for measuring thermophysical properties of ash of fossil fuel at elevated temperatures and pressures and comprises a pressure vessel means having an enclosable volume therein. Heating means are disposed in said volume and have a vertically oriented cavity therein. Sample holding means are positionable in said cavity and are adapted to contain a sample of ash of a fossil fuel. First and second electrode means are positionable in said sample holding means for respectively contacting vertically spaced apart first and second surface portions of said sample of ash when the sample of ash is contained in said sample holding means. Circuit means are coupled to said first and second electrode means for determining the resistivity of said sample of ash when subjected to said elevated pressures and temperatures. Transducer means are adapted to contact a surface of said sample of ash when contained in said sample holding means for detecting volume changes in said sample of ash when subjected to said elevated pressures and temperatures which are provided by pressurizing said volume in the pressure vessel means and actuating said heating means.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the accompanying drawings which are given by way of illustration only, and thus are not limitative of the present invention, and wherein.

DETAILED DESCRIPTION OF THE INVENTION

Figure 1:
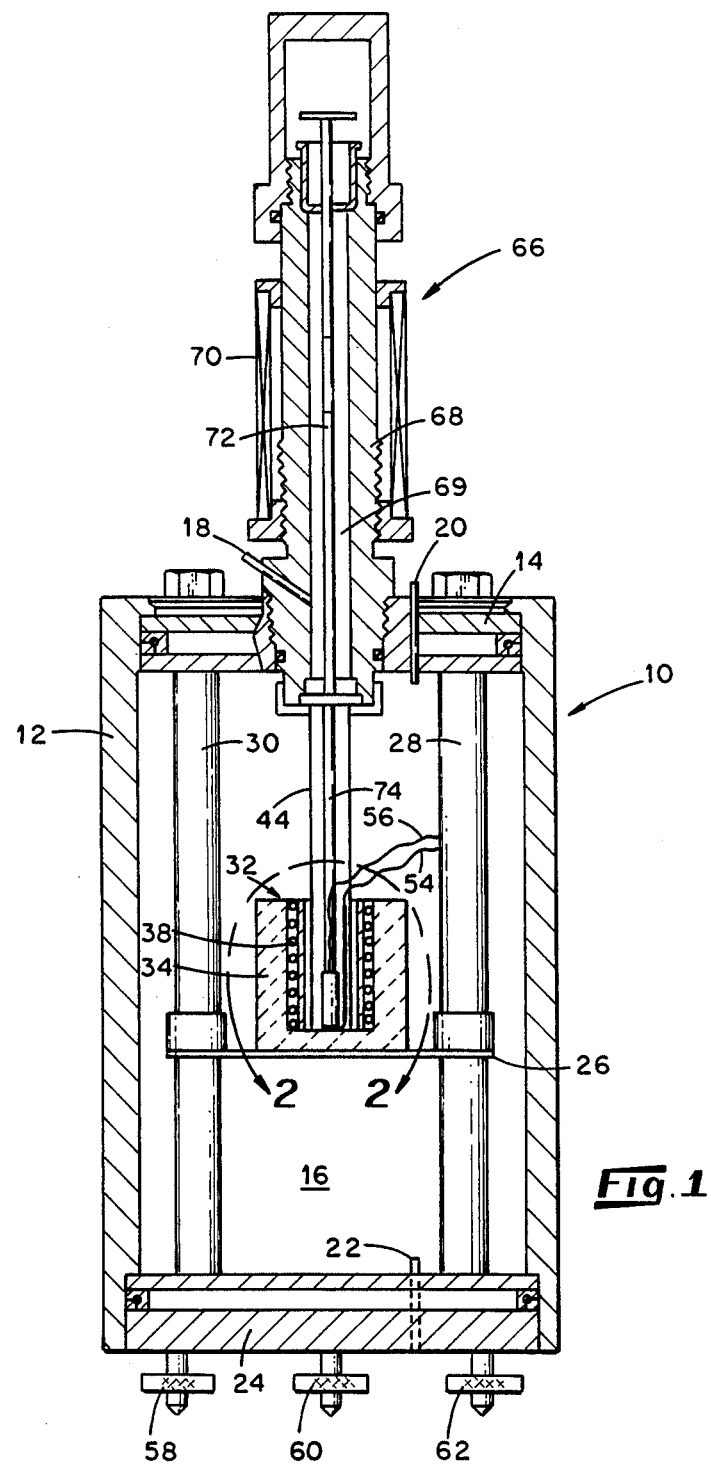
FIG. 1 is a schematic sectional view of a preferred embodiment of the apparatus of the present invention.
Figure 2:
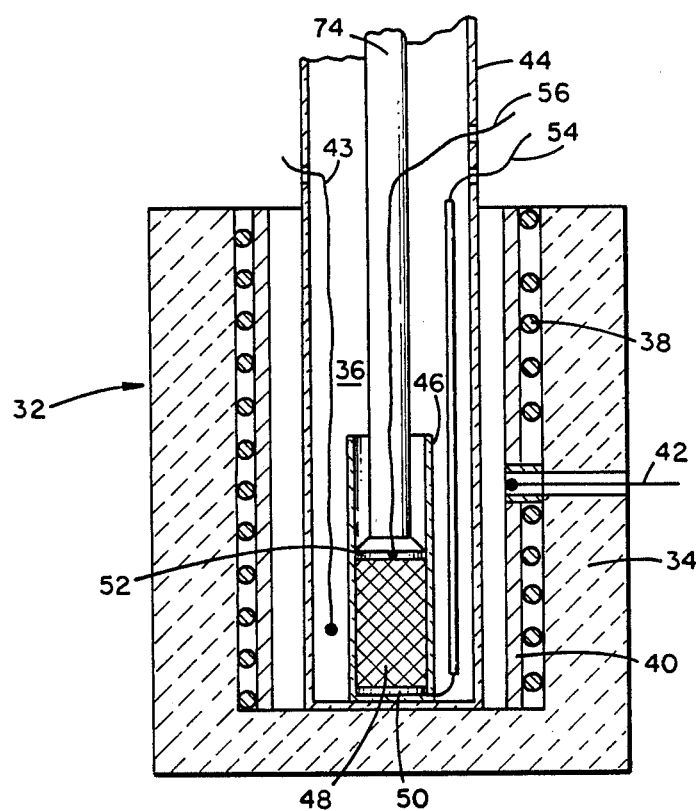
FIG. 2 is a sectional view taken along lines 2—2 of FIG. 1 showing details of the sample holder arrangement for the coal ash to be analyzed.
Figure 3:
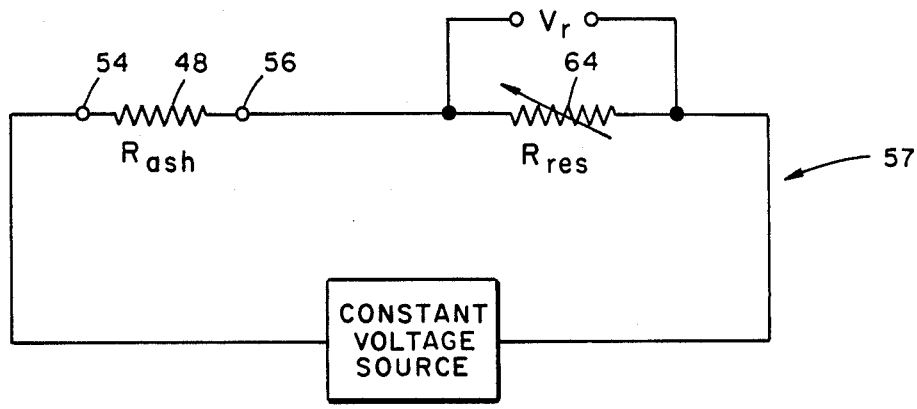
FIG. 3 is an electrical circuit coupled to the electrodes contacting the coal ash for measuring the resistivity of the coal ash.

The apparatus of the present invention is utilized for determining the sintering and fusion properties of various types of coal ash at elevated temperatures and pressures under the influence of an inert, reducing or oxidizing atmosphere. As shown in FIGS. 1 through 3, the apparatus is a microdilatometer generally indicated at 10 which comprises a pressure vessel 12 capable of being pressurized with a suitable gas to a pressure up to about 1250 psi. The pressure vessel 12 may be provided with water cooling coils (not shown). The pressure vessel 12 is provided with a removable cover 14 which permits access to an enclosable volume 16 within the pressure vessel 12. Inlet lines 18 and 20 are provided for charging the pressure vessel volume 16 with a suitable pressurized gaseous atmosphere such as one formed of air, oxygen, hydrogen, carbon monoxide, carbon dioxide, nitrogen, helium, or steam as well as mixtures thereof. The gaseous charge within this volume 16 can be exhausted or vented through either of these lines 18 or 20 or through a suitable exhaust line 22 shown in the base 24 of the pressure vessel 12. The location and number of these lines 18, 20 and 22 are not critical and can be suitable varied.

The pressure vessel volume 16 is shown provided with a horizontally disposed plate 26 carried by vertically oriented supports 28 and 30, which extend between the cover 14 and the base 24 of the pressure vessel 12. This plate 26 is vertically positionable along the supports 28 and 30 and is used to support a heating mechanism such as a resistance furnace 32 for heating the sample of coal ash to the desired elevated temperature needed for determining sintering and fusion properties of the ash. This furnace 32 may be of any suitable construction and is shown comprising a cup-shaped body of thermal insulation such as alumina with an centrally located cavity 36. Resistance heating wires 38 for the furnace are shown wound about an alumina or quartz tube 40 and disposed within the cavity 36 along essentially the entire vertical length thereof for uniformly heating the cavity volume and the material placed therein. The tube 40 supports the heating wires and also defines the working volume within the furnace cavity 36. Suitable thermocouples 42 and 43 as best shown in FIG. 2 respectively project through the insulation 34 and the alunina or quartz tube 40 and into the cavity 36 from the open end thereof for monitoring and providing a signal of the furnace temperature to a suitable control mechanism (not shown) which is utilized to regulate the temperature within the furnace cavity 36. The furnace 32 may be resistance heated to provide heat within the first cavity at a maximum rate of about 400° C. per minute to a maximum temperature of about 1,200° C. which is sufficiently high for determining the sintering and fusion properties of any coal ash.

In order to measure the sintering and fusion temperature of coal ash a sample of the ash is heated in the furnace cavity while the pressure vessel volume 16 is at a selected elevated pressure. While the ash sample is being heated, resistivity and conductivity measurements as well as expansion and contraction measurements are made on the ash sample. These measurements determine the influence of pressure with various atmospheres on the sintering and fusion properties of coal ash.

To provide for the measurements of the sintering and fusion temperature of ash of a particular coal, a closed-bottom tubular sample holder 44 is positionable within the furnace cavity 36 and vertically extends there from to a location adjacent to the cover 14 of the pressure vessel 12 where the upper end of the sample holder 44 bears against a surface of an ash expansion and contraction measuring mechanism as provided by a linear variable differential transducer (LVDT) to be described in detail below.

A vial 46 of a suitable material such as quartz is utilized for containing the ash sample generally shown at 48 for the sintering and fusion temperature measurements. This vial 46 is positionable within the sample holder 44 against the base or closed end thereof. This ash sample should contain an adequate quantity of discrete ash particulates so that sufficient physical changes in the ash will occur during sintering and fusion thereof so as to permit taking the measurements required for providing the data indicative of sintering and fusion temperatures of the particular coal ash at different elevated pressures and atmospheres. Normally a quantity of coal ash in the range of about 100 to 400 milligrams is adequate in the apparatus of the present invention for obtaining the desired measurements. The ash sample is preferably compacted to a density of about 1.2 to 2.0 of theoretical density for the particular ash. Packing the ash particulates to a density of about 1.46 grams per cubic centimeter is usually sufficient. This compaction is achieved by using any convenient mechanism such as a tamping rod.

To provide the measurements of changes in resistivity/conductivity of the coal ash during the heating thereof to determine the influence of pressure on ash sintering and fusion, the ash sample is positioned between and contacted by two disk-shaped electrodes 50 and 52. Electrode 50 can be attached to and carried on the base of the sample vial 46. Electrode 52 on the other hand is placed in contact with the uppermost side of the coal ash sample which is opposite the side contacted by the electrode 50. If desired the base of the sample vial 46 can be formed of a material suitable to provide the electrode 50. Satisfactory results have been achieved by using platinum as the electrode material for both electrodes 50 and 52.

Wire leads 54 and 56 are coupled to the electrodes 50 and 52 and extend to a resistivity meter 57 as schematically shown in FIG. 3. These wire leads 54 and 56 and leads to the thermocouples 42 and 43 may pass through suitable openings in the sidewalls of the sample holder 44 and are coupled to terminals which permit these leads to pass through the walls of the pressure vessel. For example, as shown in FIG. 1 terminals 58, 60 and 62 at the base of the pressure vessel may be used for providing the connections to the internal leads for transmitting signals to the external circuitry used for controlling and measuring the events within the pressure vessel. The thermocouples 42 and 43 are connected to a suitable conventional furnace control mechanism (not shown) while the electrode lead wires 54 and 56 are connected to the resistivity meter 57 which is utilized for determining the sintering temperature of the ash by resistivity measurements as will be discussed in detail below. The ash sample 48 acts as a resister during the resistivity measurements and completes the circuit between the electrodes 54 and 56. The resistance of the ash sample 48 varies during heating under the influence of pressure with this resistance decreasing as sintering and fusion occurs. A variable resister 64 is connected in series with the ash sample 48 and a constant voltage "V" from the voltage from the source shown in FIG. 3 is applied to this series circuit. The voltage drop ($V_r$) across the variable resistor 64 is measured and from the Ohm's law the current "I" through the circuit can be calculated:

$$I = V_r/R_{res}$$

where $R_{res}$ is the resistivity of the variable resistor 64.

After the current through the circuit has been determined Ohm's Law can then be used to calculate the total resistivity of the circuit ($R_T$) since the resistors are in series $R_{ash} = R_T - R_{res}$. With the variable resistor 64 adjusted to provide a small voltage drop thereacross the $R_{ash} > R_{res}$ can be simply calculated by the equation:

$$R_{ash} = V/I$$

where "V" is the constant voltage applied to the circuit. The voltage drop across resistor 64 is indicative of the resistivity of the ash sample 48 at the selected temperature and pressure.

In addition to the resistivity measurements the volume changes of the ash sample 48 are measured to provide a further determination as to the temperature at which sintering and fusion of the ash occurs. As the sintering of the ash is initiated, the density of the ash compact increases and the volume thereof decreases. The changes in the volume of the ash sample 48 can be accurately measured on a time-temperature-pressure basis by employing a linear variable differential transformer (LVDT) generally shown at 66. The LVDT 66 is supported by and extends through a suitable opening the pressure vessel cover 14. The LVDT is shown comprising a vertically extending cylindrical housing 68 which is threaded attached to the cover 14 and is vertically adjustable with respect thereto. The cylindrical housing 68 is provide with longitudinal passageway 69 and is vertically adjusted so that the lower most portion or end thereof will bear against the upper end of the sample holder 44 when the coal the ash sample 48 is in place so that any movement detected by the LVDT 66 occurring in the vessel is due to volume changes in the ash sample 48. The coil utilized to receive the signal indicative of vertical movement within the LVDT is shown generally at 70 and it selectively positionable on the cylindrical housing 68. This coil 70 detects and provides a signal indicative of any vertical displacement of a ferrous core 72 disposed within the passageway 69. This core 72 is attached to one end of a vertically movable probe or rod 74 which extends into the passageway 69 of the cylindrical housing 68 and into a significant length of the sample holder 44 to contact the top of the ash sample 48. The upper electrode 52 of the resistivity measuring circuit may be affixed to the distal or lower most end of the probe 74 contacting the top surface of the ash sample 48 to assure contact is maintained between the electrode 52 and the ash sample 48 during any volume changes occurring therein.

Displacement of the probe and the ferrous core 72 attached thereto due to any changes in volume of the coal ash sample 48 is detected by the coil 72. As with conventional linear variable displacement transducers a 2.5 kHz drive signal may be provided by conventional circuitry (not shown). The LVDT is preferably provided with a linear range of about ±0.5 inches for assuring accurate measurement of the volume changes in the ash sample during sintering.

In order to provide a more facile understanding of the present invention, Examples are set forth below and directed to the measurement of the sintering and fusion properties of different coal ashes at various temperatures and pressures to illustrate the changes in sintering occurring due to the influence of pressure and atmospheres at elevated temperatures. The coal ash utilized to illustrate the effect of various atmospheres such as air and helium and mixtures thereof at pressures at ambient to 500 psig were prepared from North Dakota Lignite (PSOC 1507) and Illinois No. 6 (PSOC 1493). A quantity of each of these coals were prepared by grinding the coal and grinding it to a size of −74 microns. These coal particulates were then converted to ash in a muffle furnace in an air atmosphere at 700° C. The compositions of the coal expressed as percent oxides are presented in the Table below.

TABLE

Oxide Compositions of High Temperature Coal Ash Used In Examples I an II (Ash Derived from PSOC Coals)

| Oxide | PSOC Coal No. 1943 | PSOC Coal No. 1507 |
|---|---|---|
| $SiO_2$ | 41.2 | 19.7 |
| $Al_2O_3$ | 15.7 | 9.34 |
| $TiO_2$ | 0.76 | 0.37 |
| $Fe_2O_3$ | 23.9 | 12.9 |
| MgO | 0.90 | 5.33 |
| CaO | 7.39 | 23.2 |
| $Na_2O$ | 0.40 | 5.87 |
| $K_2O$ | 1.70 | 0.69 |
| $P_2O_5$ | 0.26 | 0.34 |
| $SO_3$ | 7.90 | 20.0 |

EXAMPLE I

Figure 4:
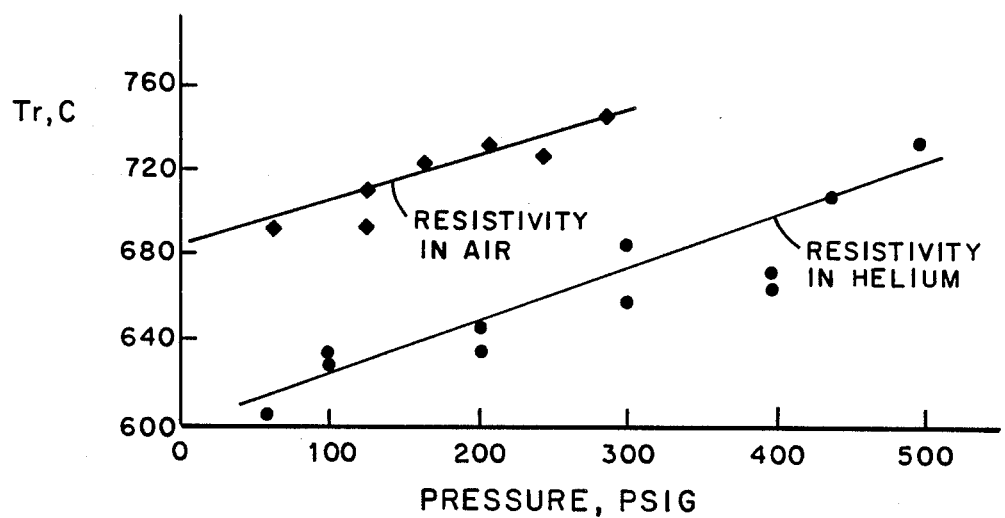
FIG. 4 is a graph illustrating the sintering temperature/pressure relationship for ash of North Dakota lignite (PSOC 1507) in air and helium.

The sintering temperature/pressure relationship for the North Dakota lignite ash is illustrated in FIG. 4. The curves in this FIG. represent sintering temperature as determined by both resistivity and shrinkage in gaseous environments provided by air and helium. The sintering temperature as determined by electrical resistivity measurements increased with increasing pressure in both air and helium. The sintering temperature in air was found to be about 80° C. greater at any given pressure than that in helium. This difference in sintering temperature was expected since alkalis present in the ash would be oxidized in air so as to yield higher melting components which result in a higher sintering temperature.

In a typical measurement utilizing the present invention the sintering temperature of the North Dakota lignite ash at ambient inert pressure occurred at 600° C. whereas at elevated pressures of 200 and 500 psig the sintering temperature was determined to be 640° C. and 740° C. These measurements show significant increases in the sintering temperature of the coal ash occurs with increases in pressure. Further, by changing the atmosphere of the sintering environment to air the sintering temperature is also changed, often by as much as about 1° C. to 80° C. when sintering occurs at the above mentioned pressure ranges.

EXAMPLE II

Figure 5:
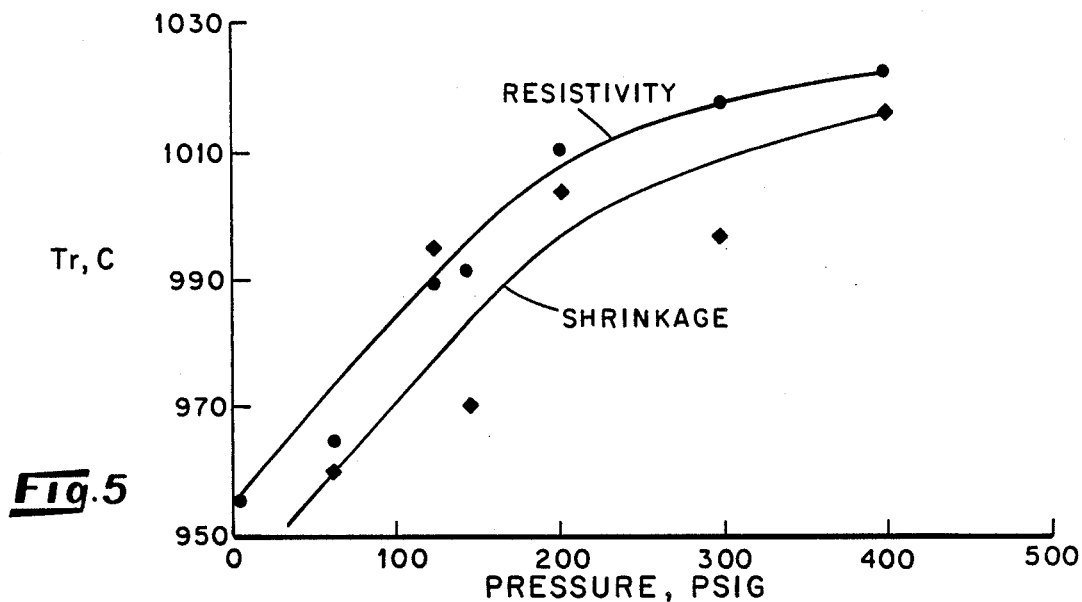
FIG. 5 is a graph illustrating the sintering temperature/pressure relationship for ash of Illinois No. 6 (PSOC 1493) in helium.
Figure 6:
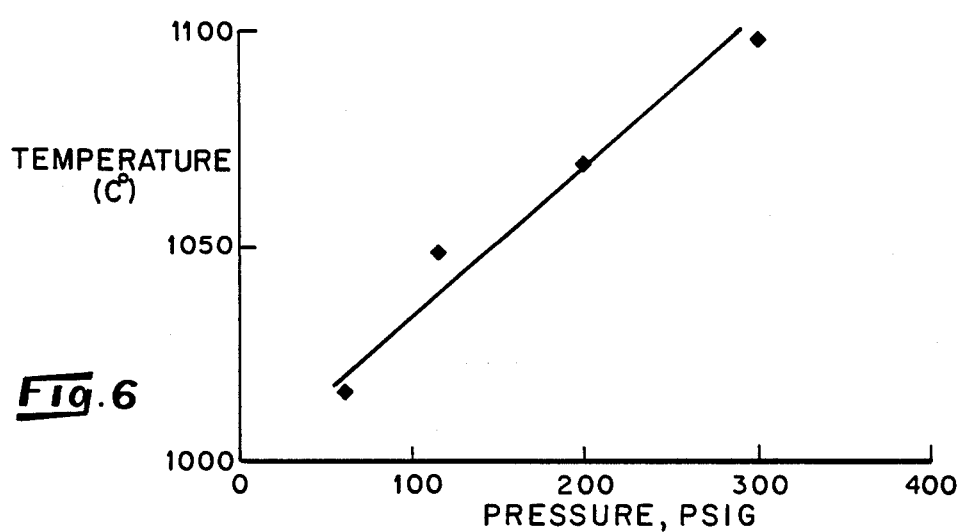
FIG. 6 is a graph illustrating the sintering temperature/pressure relationship for ash of Illinois No. 6 (PSOC 1493) in air as determined by resistivity.

The sintering/pressure relationship for Illionis No. 6 (PSOC 1493) is illustrated in FIG. 5 for a helium atmosphere and in FIG. 6 for an air atmosphere. As shown by the curves in FIG. 5 the sintering temperature as determined by resistivity measurements and by shrinkage appear to be very close at any given pressure which is expected to be due to the lower concentration of the calcium and sodium in this coal ash as compared to the North Dakota lignite ash of Example 1 and also as shown in the above Table. As indicated by the curves in FIG. 5 an essentially linear increase occurs in the sintering temperature with increasing pressure up to a pressure of about 200 psig. There was also a linear increase in the sintering temperature with an increase in pressure in an air atmosphere as shown in FIG. 6 and as determined by resistivity measurements.

Figure 7:
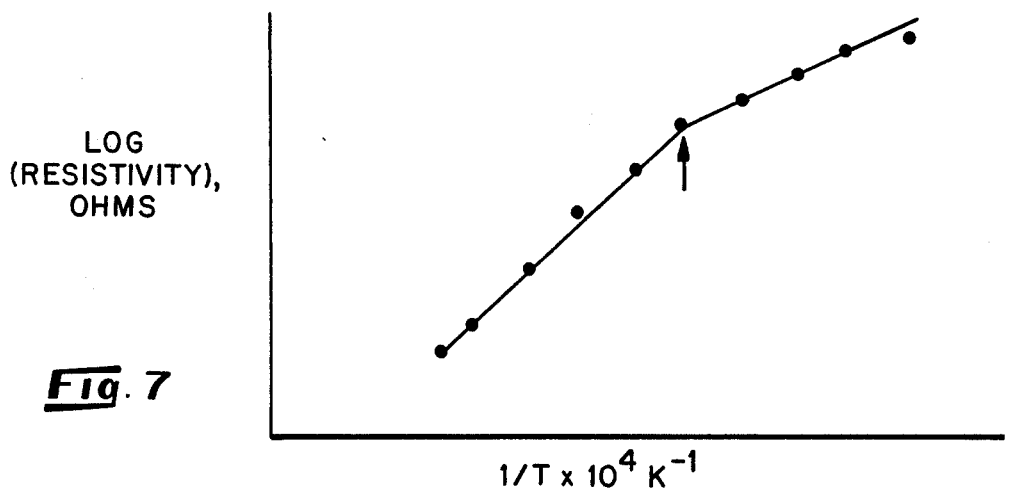
FIG. 7 is a graph illustrating the determination of sintering temperature by electrical resistivity for ash of North Dakota lignite (PSOC 1507) at 120 psig in an atmosphere of air.

In FIG. 7 the North Dakota lignite ash is utilized to provide two curves which are a plot of the log of the sampled resistance versus the reciprocal of the absolute temperature. This plot provides an illustration of how sintering temperature is determined by measuring the electrical resistivity.

It will be seen that the present invention provides a high pressure apparatus capable of determining the sintering and fusion behavior of various coal ash at elevated temperatures and pressures. The apparatus of the present invention can be utilized to clearly show that the oxidizing atmosphere provides a higher sintering temperature than in an inert atmosphere and that increases in pressure increases the sintering temperatures in both inert and oxidizing atmospheres. The sintering temperature determined by shrinkage measurements was found to decrease slightly with increased pressure due to compaction of a sample during heat treatment while the resistivity measurements appear to be more sensitive than the shrinkage measurements and perhaps may provide a better indication of the sintering temperature of coal ash.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims. For example, the subject invention could be used for determining the sintering behavior of pure minerals or ceramics. Further, electrical resistivity measurements of various materials including superconductors can be made at low temperature by injectng liquid helium or nitrogen into the pressure vessel.

What is claimed is:

1. A microdilatometer for measuring thermophysical properties of ash of fossil fuel at elevated temperatures and pressures comprising:

pressure vessel means having an enclosable volume therein;

heating means disposed in said volume and having a vertically oriented cavity therein;

sample holding means positionable in said cavity and adapted to contain a sample of ash of a fossil fuel;

first and second electrode means positionable in said sample holding means for respectively contacting vertically spaced apart first and second surface portions at opposite ends of said sample of ash when contained in said sample holding means;

circuit means coupled to said first and second electrode means for determining the resistivity of said sample of ash when subjected to an elevated pressure and temperature with said circuit means having coupled therein variable resistor means connected in series with said sample ash through said first and second electrode means, a constant voltage supply means, and meter means for measuring the voltage drop across the variable resistor means with said voltage drop being indicative of changes in the resistivity in the sample of ash when the latter is subjected to said elevated temperature and pressure; and transducer means adapted to contact a surface of said sample of ash when contained in said sample holding means for detecting volume changes in said sample of ash when subjected to said elevated pressure and elevated temperature provided by pressurizing said volume in the pressure vessel means and actuating said heating means.

2. A microdilatometer as claimed in claim 1, wherein said sample holding means comprises an elongated tubular housing disposed in said cavity with a portion thereof extending into said volume of the pressure vessel means, wherein vial means having a closed bottom end adapted to contain said sample of ash are disposed in the elongated tubular housing, wherein said first electrode means are disposed in said vial means adjacent to said closed bottom end in a contacting relationship with one end of said sample of ash, and wherein said second electrode means are affixed to an end of said rod means and are maintained in a contacting relationship with an end of said sample of ash opposite said one end by said rod means during volume changes in said sample of ash.

* * * * *